United States Patent [19]
Klopotek

[11] Patent Number: 6,056,739
[45] Date of Patent: May 2, 2000

[54] PROFILING THE INTENSITY DISTRIBUTION OF OPTICAL BEAMS

[75] Inventor: Peter J. Klopotek, Framingham, Mass.

[73] Assignee: Summit Technology, Inc., Waltham, Mass.

[21] Appl. No.: 08/748,048

[22] Filed: Nov. 12, 1996

Related U.S. Application Data

[63] Continuation of application No. 08/226,662, Apr. 8, 1994, abandoned.

[51] Int. Cl.⁷ .................................................. A61N 5/06
[52] U.S. Cl. .................................. 606/5; 606/3; 606/10; 606/13; 606/17; 359/851
[58] Field of Search ...................... 606/2, 3–19; 359/851, 359/853

[56] References Cited

U.S. PATENT DOCUMENTS

| | | | |
|---|---|---|---|
| 3,670,260 | 6/1972 | Koester et al. | 606/10 |
| 3,941,973 | 3/1976 | Luck, Jr. et al. | 219/121.6 |
| 4,315,130 | 2/1982 | Inagaki et al. . | |
| 4,484,334 | 11/1984 | Pressley | 359/853 |
| 4,669,466 | 6/1987 | L'Esperance | 606/5 |
| 4,733,944 | 3/1988 | Fahlen et al. | 350/167 |
| 4,856,513 | 8/1989 | Muller | 128/303.1 |
| 4,911,711 | 3/1990 | Telfair et al. | 606/11 |
| 4,941,093 | 7/1990 | Marshall et al. | 364/413.01 |
| 4,994,058 | 2/1991 | Raven et al. | 606/5 |
| 5,019,074 | 5/1991 | Muller | 606/5 |
| 5,091,626 | 2/1992 | Lewis et al. | 219/121.69 |
| 5,163,934 | 11/1992 | Munnerlyn | 606/5 |
| 5,312,320 | 5/1994 | L'Esperance, Jr. | 606/5 |

FOREIGN PATENT DOCUMENTS

| | | |
|---|---|---|
| 0 080 597 | 12/1986 | European Pat. Off. . |
| 2 180 363 | 3/1987 | United Kingdom . |

OTHER PUBLICATIONS

Bruno et al., "Laserbeam Shaping for Maximum Uniformity and Minimum Loss", *Lasers& Applications*, pp. 91–94 (Apr. 1987).

Deng, et al., "Uniform illumination of large targets using a lens array", *Applied Optics*, 25:377–381 (Feb. 1986).

Iwasaki et al., "Flattening Laserbeam Intensity Distribution", *Lasers & Applications*, pp. 76–78 (Apr. 1983).

Han et al., "Reshaping collimated laser beams with Gaussian profile to uniform profiles", *Applied Optics* 22:3644–3647 (Nov. 1983).

Rhodes et al., "Refractive optical systems for irradiance redistribution of collimated radiation: their design and analysis", *Applied Optics*, 19:3545–3553 (Oct. 1980).

Lacombat et al., "Laser Projection Printing", *Solid State Technology*, pp. 115–121 (Aug. 1980).

Grojean et al., "Production of flat top beam profiles for high energy lasers", *Rev. Sci. Instrum.*, 51:375–376 (Mar. 1980).

Horton et al., "Design of a Specular Aspheric Surface to Uniformly Radiate a Flat Surface using a Nonuniform Collimated Radiation Source", *Journal of Heat Transfer*, pp. 453–458 (Nov. 1972).

emphasis™ Erodible Mask brochure (May 1993).

(List continued on next page.)

*Primary Examiner*—David M. Shay
*Attorney, Agent, or Firm*—Thomas J. Engellenner; Nutter, McClennen & Fish, LLP

[57] ABSTRACT

A beam profiler comprising: an intensity modifier constructed and arranged to separately modify the intensity profile of different subbeam portions of an initial beam to thereby create respective subbeams each having a respective predetermined modification; and a subbeam-directing optical system constructed and arranged to direct the multiple subbeams along respective subbeam beam paths that substantially overlap in an overlap plane, whereby, a resulting beam of radiation is created at the overlap plane that has an intensity profile equal to the optical incoherent summation of the predetermined intensity profiles of said overlapping subbeams. The intensity modifier preferably comprises an array of intensity-modifying profiling elements disposed across the initial beam each producing a corresponding subbeam.

27 Claims, 12 Drawing Sheets

OTHER PUBLICATIONS

Bor et al., "Physical problems of excimer laser cornea ablation", *Optical Engineering*, 32:2481–2486 (Oct. 1993).

Morrill, "Theories presented on PRK's 'central islands'", *Ocular Surgery News*, pp. 26–27 (Sep. 15, 1993).

Wright, "Corneal Islands Minimized by Latest Refinements", *Opthalmology Times*, (Sep. 15, 1993).

Piebenga, et al., "Excimer Photorefractive Keratectomy for Myopia", *Opthalmology*, 100:1335–1345 (Sep. 1993).

Krueger, et al., "Corneal Surface Morphology Following Excimer Laser Ablation With Humidified Gases", *Arch Ophthalmol*, 111:1131–1137 (Aug. 1993).

Tabat et al., "Profile characteristics of excimer laser micromachined features", *SPIE*, 1835:144–157 (1992).

Ozaki et al., "Cylindrical fly's eye lens for intensity redistribution of an excimer laser beam", *Applied Optics*, 28:106–110 (Jan. 1989).

PROFILING THE INTENSITY DISTRIBUTION OF OPTICAL BEAMS

This application is a continuation of application Ser. No. 08/226,662, filed on Apr. 8, 1994, abandoned, entitled PROFILING THE INTENSITY DISTRIBUTION OF OPTICAL BEAMS.

BACKGROUND

This invention relates to profiling the intensity distribution of optical beams.

Various schemes have been developed for controlling the amount of optical energy received by a target surface to achieve e.g., a desired ablation profile, or a desired profile of optical exposure.

For example, many photorefractive keratectomy (PRK) procedures require the delivery of a precise dose of optical energy to the cornea of a patient's eye suffering from e.g., myopia or hyperopia to remove corneal tissue in a controlled fashion to shape the surface of the cornea to change the radius of curvature, or refractive power, of the patient's eye.

The cornea comprises transparent avascular tissue that forms the anterior portion of the eye. The cornea functions as both a protective membrane and a "window" through which light passes as it proceeds to the retina. The transparency of the cornea is due to its uniform structure, avascularity, and deturgescence, which is the state of relative hydration of the corneal tissue. The average adult cornea is about 0.65 mm thick at the periphery, and about 0.54 mm thick in the center. From anterior to posterior, the cornea has the following five distinct layers: the epithelium, Bowman's membrane, the stroma, Descemet's membrane, and the endothelium.

A major proportion of the refractive power of the eye is determined by the curvature of the anterior surface of the cornea, so that changing the shape of the cornea offers a way to significantly reduce or eliminate a refractive error in the eye.

The general technique for shaping the cornea of a patient's eye involves removing the epithelial layer, and then shaping the underlying Bowman's and stroma layers, either surgically, or by using photoablation with e.g., ultraviolet radiation from an excimer laser or infrared laser radiation from an infrared laser operating at a wavelength of about 2.6–3.2 $\mu$m.

In radial keratotomy, a set of radial incisions are made in the stroma to change the eye curvature, as described in Schneider et al. U.S. Pat. No. 4,648,400.

Another technique, described in Muller, U.S. Pat. No. 4,856,513 (assigned to the present assignee), uses a laser and an erodible mask with a predefined profile of resistance to erosion by laser radiation disposed between the laser and the corneal surface. A portion of the laser radiation is absorbed by the mask, while another portion is transmitted to the corneal surface in accordance with the mask profile, thereby selectively photoablating the corneal surface into a desired shape.

In yet another technique, described in Marshall et al., U.S. Pat. No. 4,941,093 (assigned to the present assignee), the shape and size of the area of the corneal surface irradiated by laser energy is selected and controlled with an adjustable aperture or lens so that some areas of the corneal surface become more ablated than other areas, whereby a desired corneal shape can be achieved.

Alternatively, the cornea can be shaped by controllably scanning laser beams across the corneal surface, which have small spot sizes relative to the size of the ablation area.

Many conventional photorefractive keratectomy (PRK) procedures employ laser radiation from an excimer laser. However, a laser pulse from an excimer laser generally has a nonuniform intensity profile, and its beam diverges more than most lasers.

A typical excimer laser, operating at 193 nm, has an intensity profile that is about 8 mm by 24 mm with a gaussian distribution across the short dimension and ±10% intensity variation across the long dimension, and has an intrinsic divergence of about 1 milli-radian.

The ultimate commercial success of PRK will be determined by the predictability, stability, and safety of the procedure.

A simple, reproducible laser ablation technique could complement or replace the above-mentioned techniques and could further advance the field of corneal shaping.

SUMMARY

The invention concerns an optical beam profiler and a method of beam profiling for creating a beam of radiation having a desired intensity profile from an initial radiation beam.

As used herein, the terms "intensity distribution" and "intensity profile" refer to the distribution of the intensity of photoablating radiation over the cross-section of the beam.

In one general aspect, the invention features a beam profiler comprising: an intensity modifier constructed and arranged to separately modify the intensity profile of different subbeam portions of the initial beam to thereby create respective subbeams each having a respective predetermined modification; and a subbeam-directing optical system constructed and arranged to direct the multiple subbeams along respective subbeam beam paths that substantially overlap in an overlap plane, whereby, a resulting beam of radiation is created at the overlap plane that has an intensity profile equal to the optical incoherent summation of the modified intensity profiles of the overlapping subbeams, the intensity profile of the resulting beam corresponding to the desired intensity profile.

As used herein, the term optical incoherent summation means that the intensity at any given location in the overlap plane results from an incoherent sum of the respective portions of the contributing subbeams, and that interference effects can be neglected.

Because the desired filtering function is applied to different subbeam portions of the initial radiation beam, which are then optically summed at the overlap plane, the resulting beam has an intensity profile that has much smaller intensity variations than the initial beam.

Furthermore, the resulting beam has an intensity profile that can be applied directly to a target surface (e.g., the corneal surface of a patient's eye, or a photoresist layer for patterning features on a semiconductor surface), and thus not require any further intervening optical devices, such as an adjustable iris or an erodible mask.

The invention is particularly valuable for use with infrared PRK systems, which cannot accurately employ an iris because each pulse of infrared radiation tends to ablate too deeply into corneal tissue.

The intensity modifier preferably comprises an array of intensity-modifying profiling elements disposed across the initial beam each substantially producing a corresponding subbeam. Each of the profiling elements preferably comprises a predetermined pattern of radiation transmissive and non-transmissive regions. Alternatively, each of the profiling elements comprises a predetermined pattern of radiation reflecting and non-reflecting regions.

In certain preferred embodiments, the patterns are constructed and arranged to produce corresponding subbeams that are modified according to substantially identical intensity modifying functions. Preferably, the patterns are configured to provide substantially identical beam-modifying functions that produce corresponding subbeams that are oriented with respect to each other in a manner characterized in that the local intensity profile variations of each of the subbeams substantially cancel in the optical incoherent summation that results at the overlap plane.

In certain other preferred embodiments, the subbeam-directing optical system is constructed and arranged to overlap the subbeams at the overlap plane a sufficient distance from the array of profiling elements for localized intensity profile variations in each of the subbeams, introduced by the profiling elements, to become substantially averaged out at the overlap plane as a result of intrinsic divergence in the initial beam of radiation.

In certain embodiments, the profiling elements in the array are substantially close-packed. Preferably, the profiling elements in these embodiments are substantially identical in size and shape.

Preferably, the patterns are configured to produce subbeams having cross-sectional shapes substantially corresponding to a desired cross-sectional shape of the resulting beam (e.g., circular).

In preferred embodiments, the optical beam profiler further comprises a subbeam delivery system for re-imaging the overlap plane onto a image plane at a target surface.

In one embodiment, the subbeam-directing optical system comprises first and second rectangular prisms oriented at ninety degrees relative to each other. In another embodiment, the subbeam-directing optical system comprises an array of lenses each constructed and arranged to receive one of the subbeams, and a second lens constructed and arranged to receive each of the subbeams, the array of lenses and the second lens being configured to substantially direct each of the subbeams to overlap in the overlap plane.

The second lens is preferably located either adjacent the array or at a distance from the array equal to about twice the focal distance of the lenses of the array.

In another aspect, the invention concerns a PRK laser ablation system for selectively ablating corneal tissue of a patient's eye in an ablation area to produce a desired corneal shape.

According to this aspect, the invention features a PRK system comprising: a source of an initial beam of radiation; a beam profiler, interposed between the source and the patient's eye, constructed and arranged to separately modify different subbeam portions of the initial beam to thereby create respective subbeams each having a respective predetermined modification and to direct the multiple subbeams along respective subbeam beam paths that substantially overlap in an overlap plane, whereby a resulting beam of radiation is created at the overlap plane that has an intensity profile selected to produce the desired corneal shape in the patient's eye.

In certain preferred embodiments, the beam profiler is constructed and arranged to produce a resulting beam having an intensity profile to ablate a shape in the corneal surface of the patient's eye suitable to treat myopia, hyperopia, or astigmatism.

In certain other preferred embodiments, the beam profiler is constructed and arranged to produce a resulting beam having an intensity profile suitable remove irregular growth on the corneal surface.

In another aspect, the invention features a method for creating a beam of radiation having a desired intensity profile from an initial radiation beam comprising the steps of: providing an initial beam of radiation along a beam path; providing an intensity modifier in the beam path of the initial beam for receiving the initial beam of radiation, the modifier being constructed and arranged to separately modify the intensity profile of different subbeam portions of the initial beam to thereby create respective subbeams each having a respective predetermined modification and providing a subbeam-directing optical system constructed and arranged to direct the multiple subbeams along respective subbeam beam paths substantially overlapping in an overlap plane, whereby, a resulting beam of radiation is created at the overlap plane having an intensity profile equal to the optical incoherent summation of the predetermined intensity profiles of the overlapping subbeams, the intensity profile of the resulting beam corresponding to the desired intensity profile.

In another aspect, the invention concerns a method of selectively ablating corneal tissue of a patient's eye in an ablation area to produce a desired corneal shape.

According to this aspect, the method comprises the steps of: (a) providing an initial beam of radiation; (b) interposing between the source and the patient's eye, a beam profiler constructed and arranged to separately modify different subbeam portions of the initial beam to thereby create respective subbeams each having a respective predetermined modification; and (d) directing the multiple subbeams along respective subbeam beam paths that substantially overlap in an overlap plane, whereby a resulting beam of radiation is created at the overlap plane that has an intensity profile selected to produce the desired corneal shape in the patient's eye.

In another embodiment according to this aspect, the method comprises the steps of: (a) measuring optical parameters of the eye; (b) selecting a desired intensity profile of an ablation beam for shaping the patient's cornea; (c) selecting an intensity modifier constructed and arranged to separately modify the intensity profile of different subbeam portions of an initial beam to thereby create respective subbeams each having a respective predetermined modification; (d) providing a subbeam-directing optical system constructed and arranged to direct the multiple subbeams along respective subbeam beam paths substantially overlap in an overlap plane, whereby a resulting beam of radiation is created at the overlap plane that has an intensity profile selected to produce the desired corneal shape in the patient's eye; (e) providing an initial beam of radiation; (f) receiving the initial beam on the intensity modifier; and (g) guiding the resulting beam of radiation to the corneal surface and ablating the corneal tissue in a manner to produce the desired corneal shape.

Preferably, the method further comprises the step of examining the shaped corneal surface.

Beam profiling according to the invention permits the PRK surgeon to accurately select a desired intensity profile, and the required number of radiation pulses, and then apply these pulses directly to the patient's eye. Thereby, providing a simple, quick, and cost-effective means for properly producing a corrective refractive shape into the patient's eye.

Other features and advantages will become apparent from the following description and from the claims.

DESCRIPTION

Figure 7:
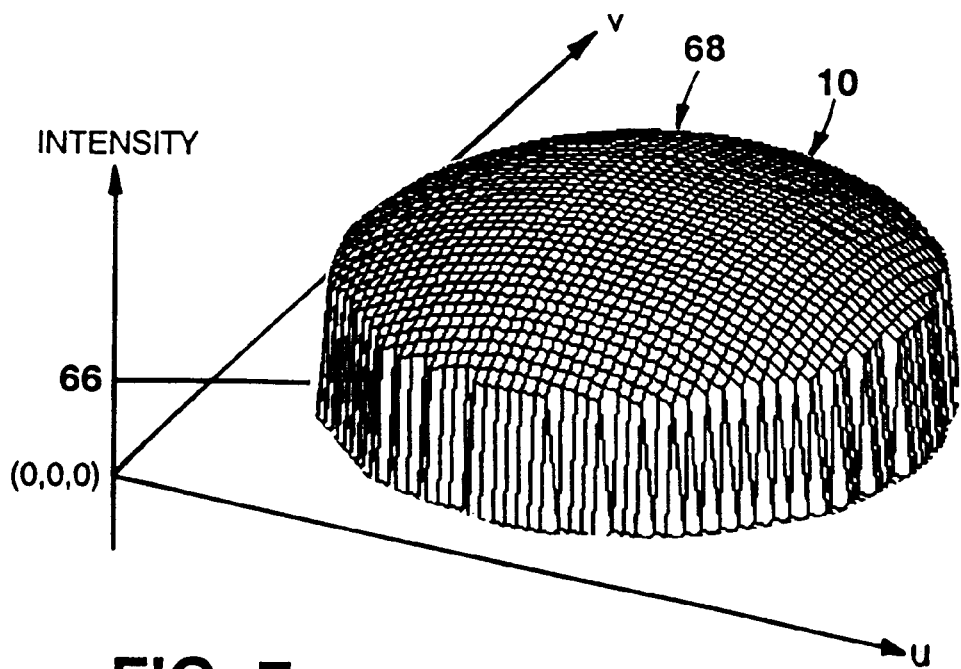
Figure 7A:
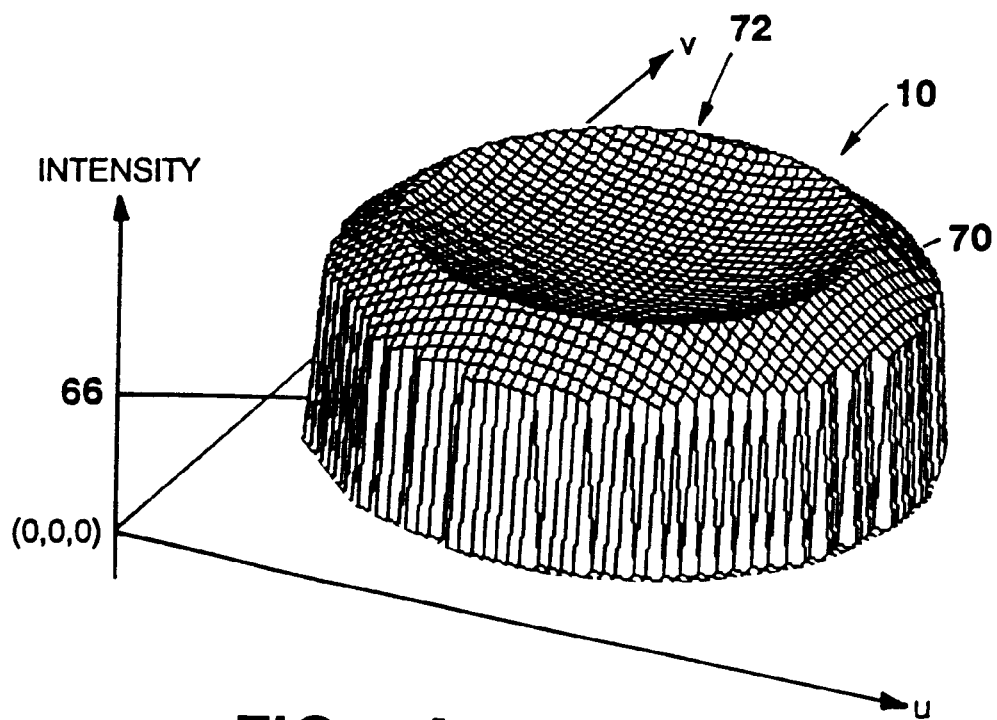
Figure 7B:
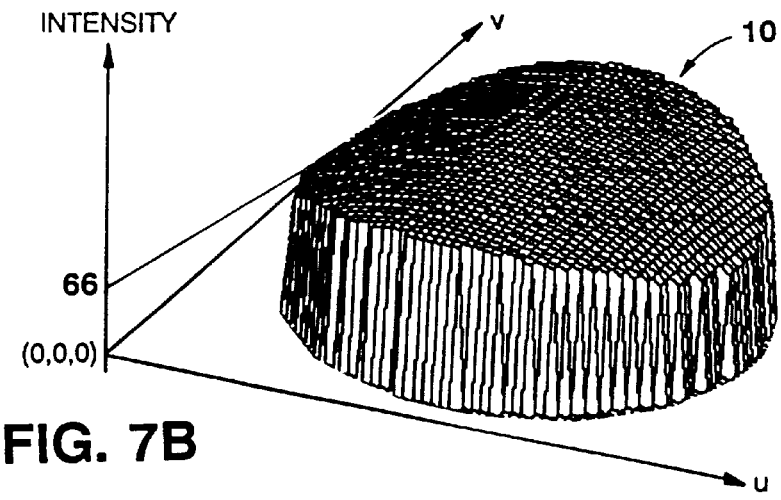
Figure 7C:
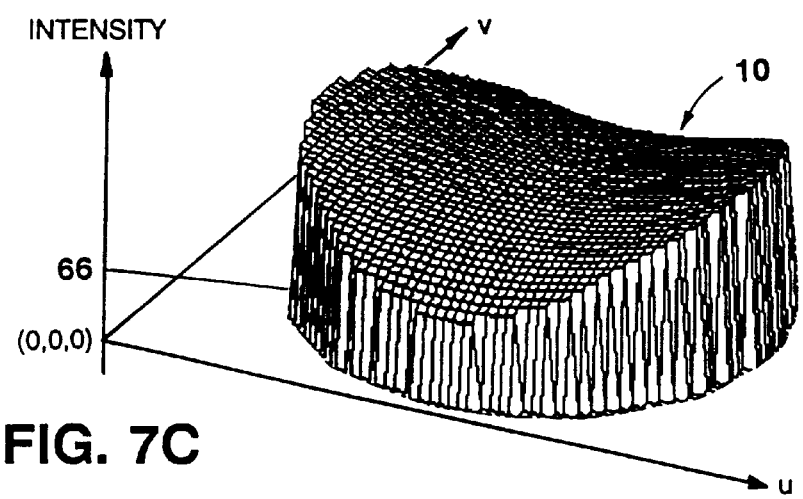
Figure 7D:
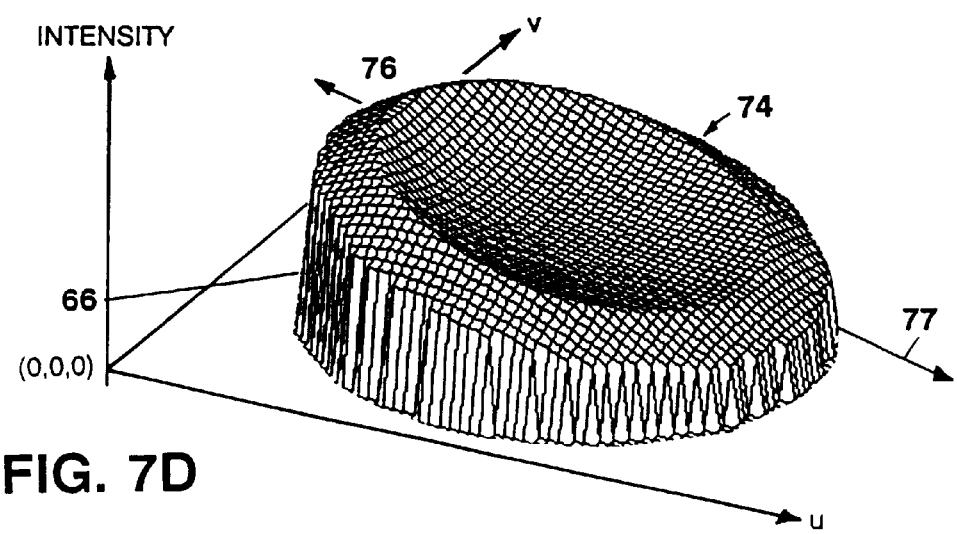

FIGS. 7 and 7A are three-dimensional graphs of desired intensity profiles of a resulting photoablation beam, created by beam profilers according to the invention, that can be used for treatment of myopia and hyperopia, respectively. FIGS. 7B and 7C show beam profiles that can be used for treatment of astigmatism having mostly myopic axial components, and hyperopic and myopic axial components, respectively. FIG. 7D shows an arbitrarily-shaped beam profile.

Figure 8:
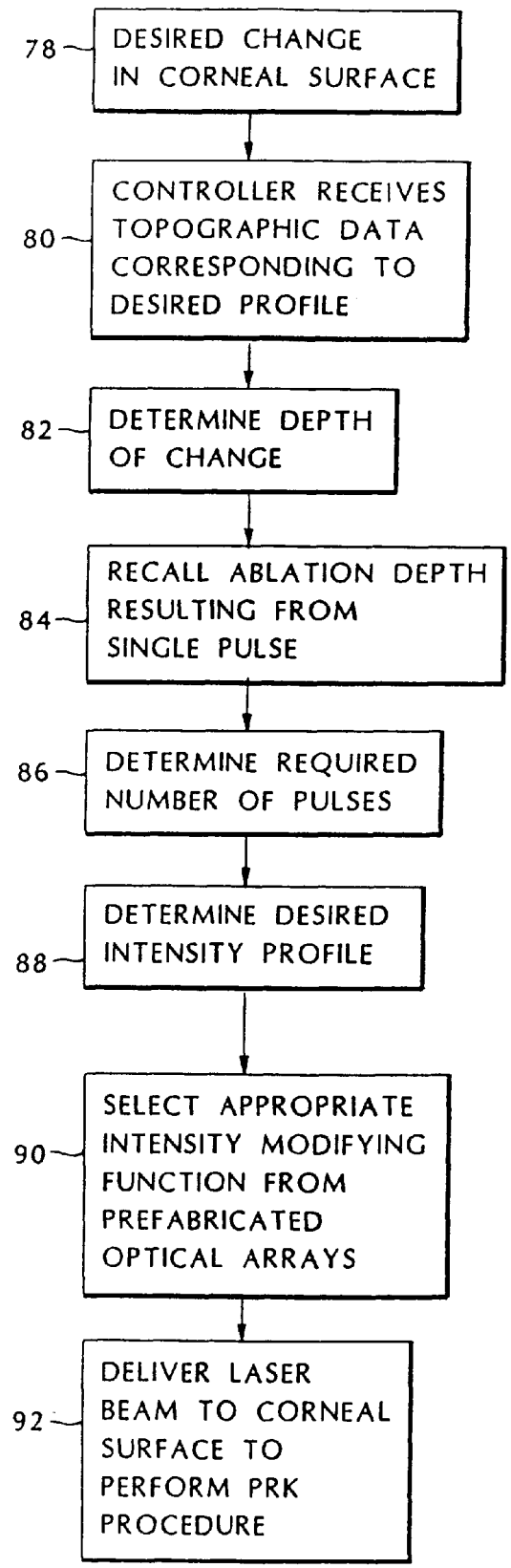

FIG. 8 is a flow diagram of a method according to the invention for performing a PRK procedure to achieve a desired correction in the cornea of a patient's eye.

Figure 9:
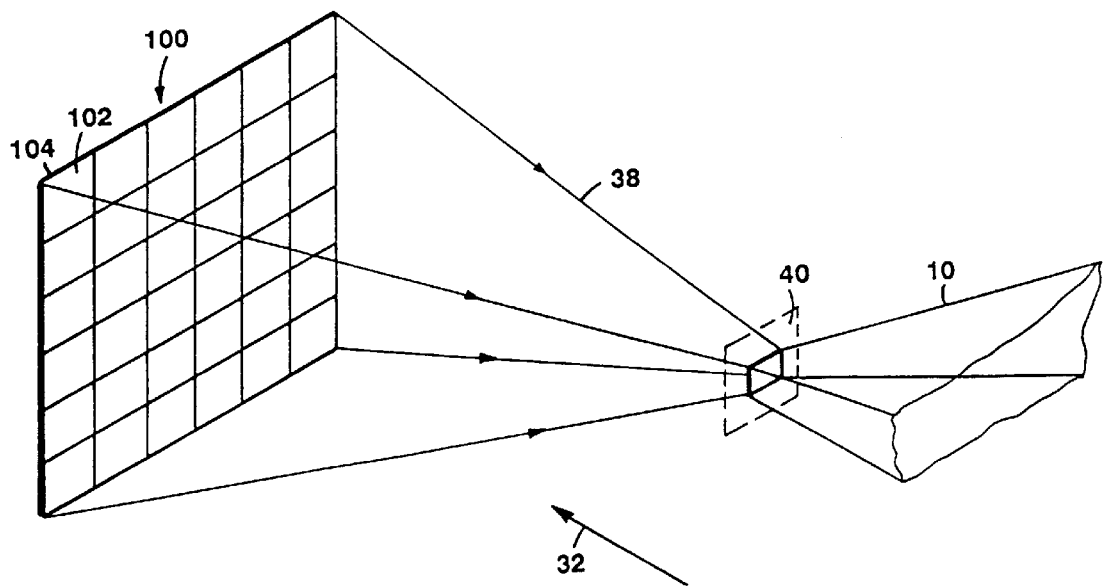

FIG. 9 is a schematic diagram of an alternative beam profiler.

Figure 1:
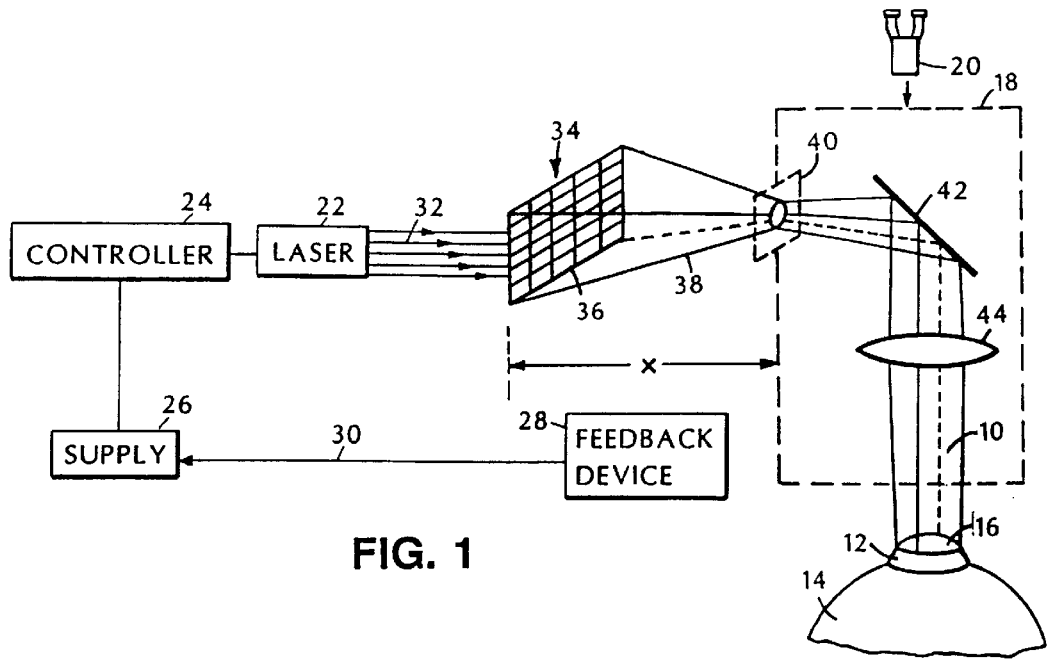
FIG. 1 is a schematic diagram of a beam profiler that modifies an initial laser beam, and a subbeam delivery system that delivers the resulting beam to the corneal surface of a patient's eye.

Referring to FIG. 1, a beam of photoablating laser radiation 10 that has a predetermined intensity profile, created by a beam profiler in accordance with the present invention, impinges on the corneal surface 12 of a patient's eye 14 in an ablation region 16 to produce a desired refractive correction in the patient's eye.

A subbeam delivery system 18 is supported above the patient's eye by an eyepiece (e.g., available from Steinway Instruments of San Diego, Calif. U.S.A). During the cornea shaping procedure, the patient's eye may be observed using a surgical microscope 20.

A laser 22 (e.g., an EXCIMED ArF excimer laser, available from Summit Technology, Inc. of Watertown, Mass. U.S.A.; although other lasers may be used, such as HF, pulsed $CO_2$, infrared lasers at wavelengths of between about 2.6–3.2 $\mu$m, Er:YSGG, and Er:YAG lasers) is controlled by a controller 24 (e.g., a commercially available microprocessor-based computer), and powered by a power supply 26. Controller 24 selectively controls the frequency and intensity of the radiation pulses from laser 22.

A feedback device 28, such as a profilometer or keratometer (e.g., a PHOTOKERATOSCOPE™ manufactured by Sun Contact Lens Company of Kyoto, Japan, or a CORNEASCOPE™ manufactured by International Diagnostic Instruments Limited, Broken Arrow, Okla. U.S.A.), sends signals to the controller via a feedback path 30, for precise control of the laser during the photoablation procedure.

Feedback device 28 also includes an energy/power meter that measures the radiant energy delivered to the corneal surface 12.

Laser 22 provides an initial beam 32 of radiation that irradiates a beam profiler 34 which includes an array of profiling elements 36.

Profiler 34 divides beam 32 into an array of subbeams 38, each of which having a one-to-one correspondence with a respective portion of the initial beam and each of which being modified from its respective portion of the initial beam as a result of interacting with a respective profiling element 36, which received that portion of the initial beam, and provides a desired beam-modifying function.

Subbeams 38, modified by profiler 34, are directed to an overlap plane 40, which can correspond to the actual ablation area 16, or preferably, as shown, subbeam delivery system 18 directs individual subbeams 38 over a desired distance from the laser to again overlap at the ablation area that is spaced a certain distance from overlap plane 40.

An aperture 39, or other optical device, is preferably located at the overlap plane to substantially eliminate fringe effects.

In beam profiling according to the invention, rather than attempting to modify the entire beam 32 according to a desired beam intensity profile, each of the profiling elements modifies only a selected portion of beam 32 according to the desired intensity profile. In this way, the intensity variation across any of the profiling elements is less than the intensity variation across the entire beam 32, and upon imaging of the subbeams in overlap plane 40, by optical incoherent summation, the undesired intensity variations in the initial beam become substantially cancelled.

Thus, a beam that has a highly reproducible, predictable and desired intensity profile can be provided which is substantially independent of the intensity variations over the cross-section of the initial laser beam.

Figure 2:
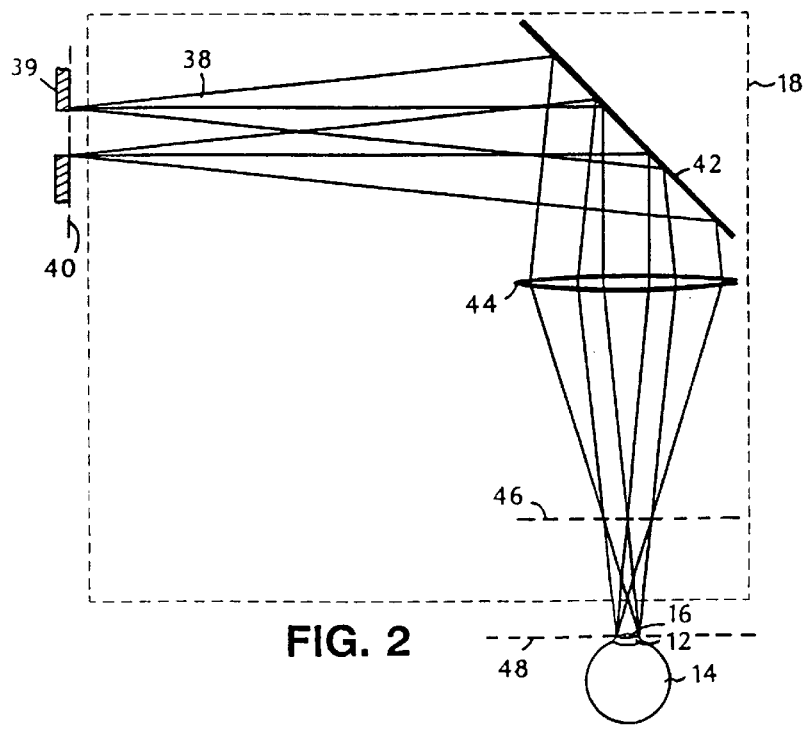
FIG. 2 is a more detailed schematic view of the subbeam delivery system of FIG. 1.

As shown in FIG. 2, subbeam delivery system 18 includes a mirror 42 and a lens 44 which focuses subbeams 38 onto a focal plane 46 and which also images the subbeams onto an image plane 48 corresponding to ablation area 16.

Subbeam delivery system 18 does not substantially alter the intensity distribution of subbeams 38, thus the intensity profile of each subbeam at overlap plane 40 is substantially the same as the intensity profile of each overlapped subbeam forming photoablating beam 10 at corneal surface 12. Beam 10 applied to the cornea substantially covers the entire ablation area 16, which generally corresponds to the portion of the corneal surface used for eyesight.

It is important that the subbeams 38 substantially overlap in overlap plane 40. This overlap depends, at least in some respects, upon the degree of spatial coherence of initial beam 32 from laser 22, which can be measured by the intrinsic divergence of the beam. Typical excimer lasers (e.g., available from Summit Technologies) provide beams which have an intrinsic divergence of about 1 milli-radian, which provides sufficient coherence to enable operation of the system in important instances.

In preferred embodiments, the distance X between profiler 34 and overlap plane 40 is selected so that the product of the intrinsic divergence of the beam and the distance X is less than the area of subbeam overlap in overlap plane 40, so that the desired level of cancellation of the variation in the initial beam intensity profile. Generally, it is preferred that this product be selected to be less than about 50% of the overlap area, and preferably this product is less than about 5–10% of the overlap area.

In preferred embodiments, the distance X is selected to be large enough so that beam distortions do not occur, such as those distortions which, for correction, would require use of so-called "fast optics."

Figure 3:
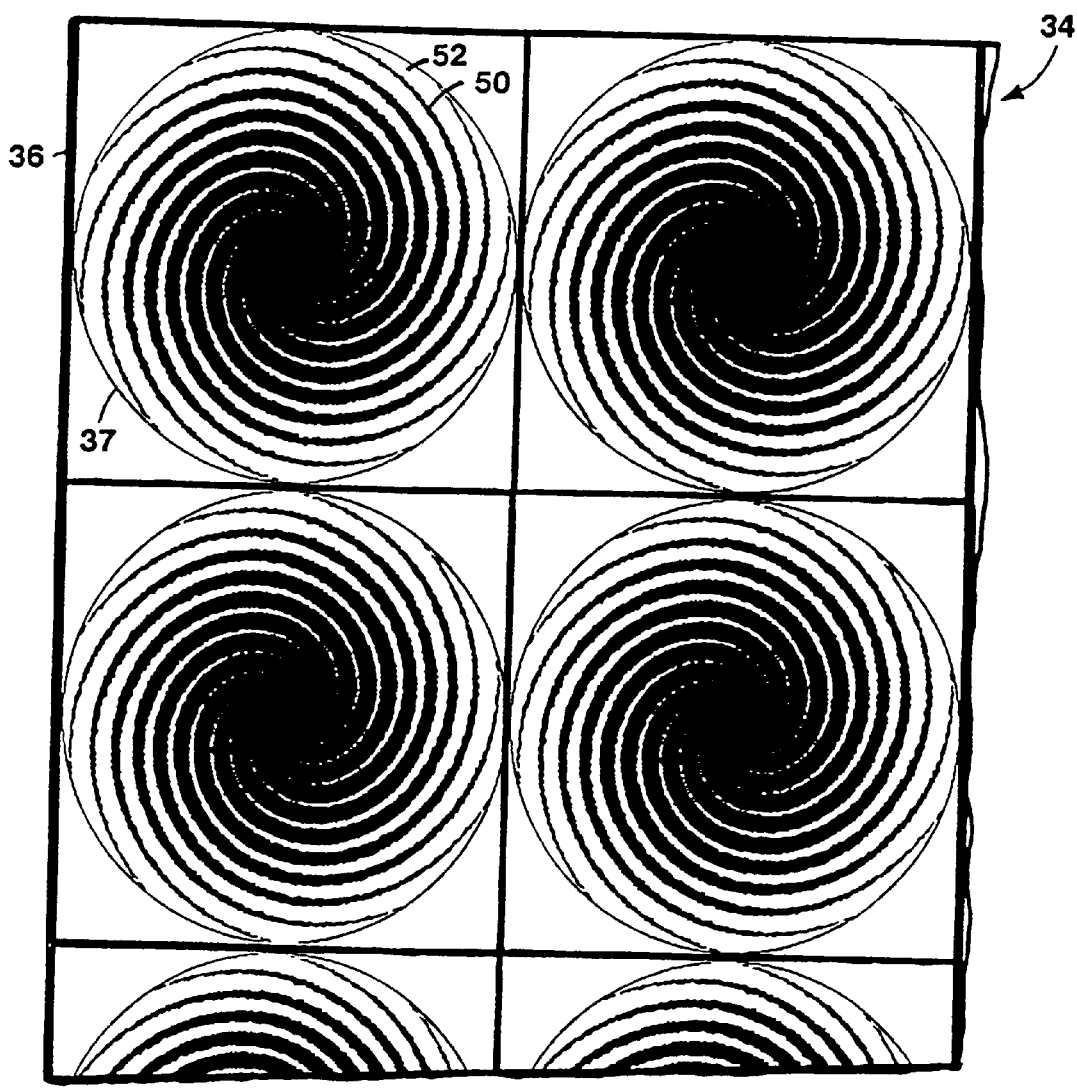
FIGS. 3 and 3A are partial schematic views of non-close-packed and close-packed arrays of intensity-defining elements, respectively.
Figure 3A:
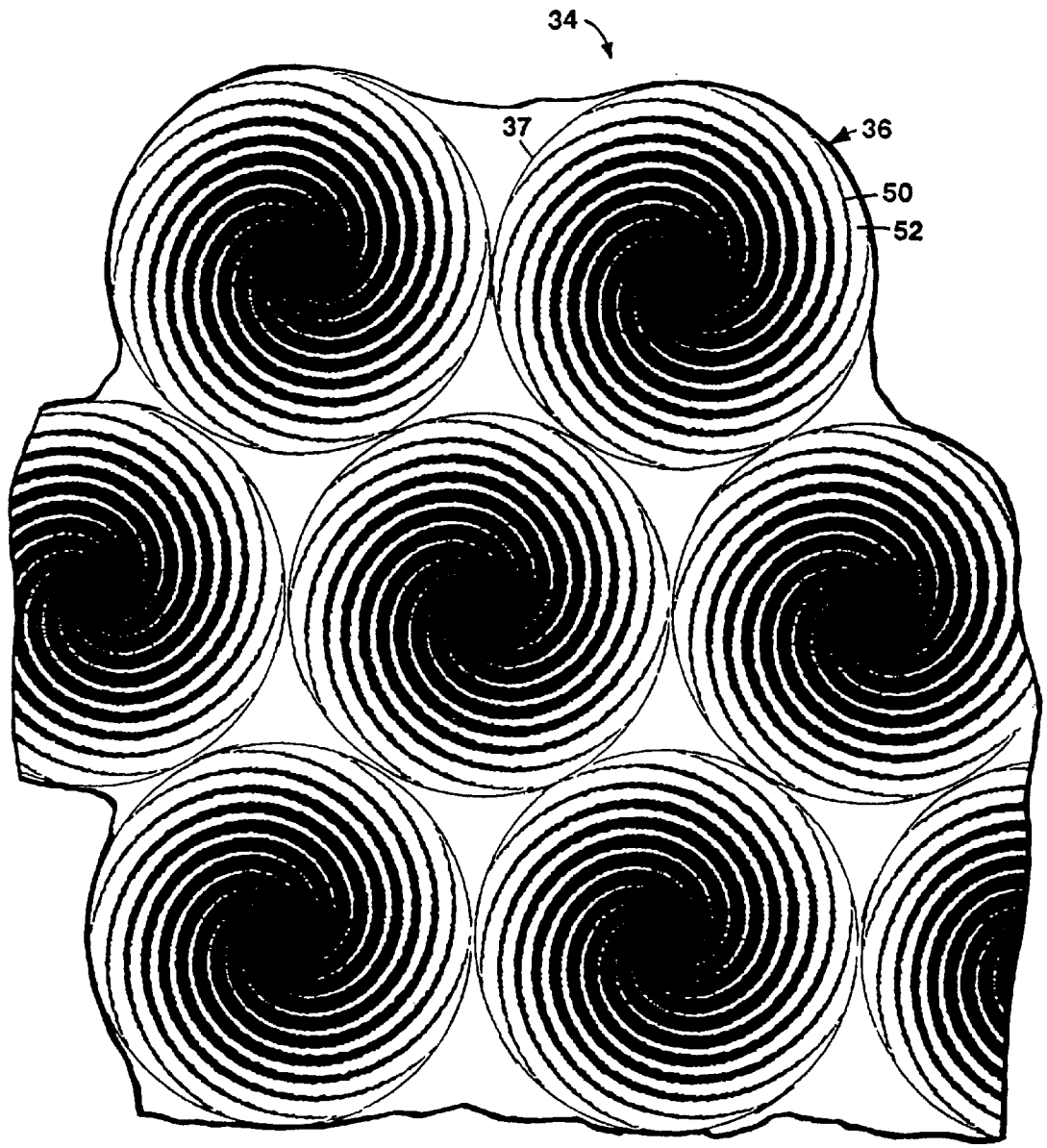

As shown in FIGS. 3 and 3A, in preferred embodiments, each optical element 36 includes an intensity-defining element 37 that comprises a predetermined pattern of light-transmissive and non-transmissive regions 50 (shown in black) and 52 (shown in white) respectively.

The predetermined pattern of each optical element is selected to correspond to the desired application.

Figure 4:
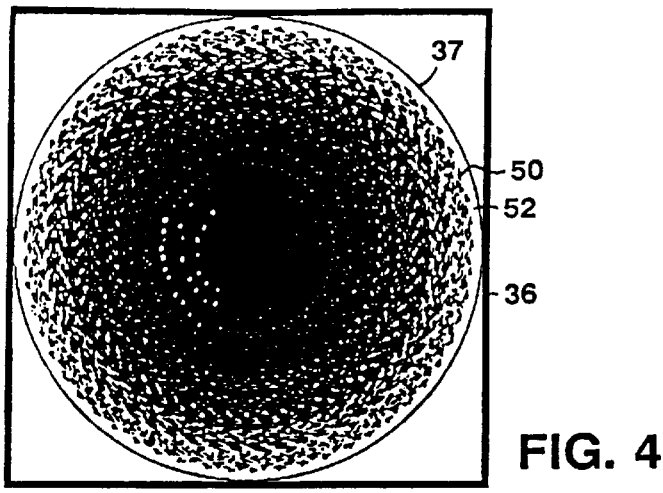
FIGS. 4–4B are schematic views of alternative intensity-defining elements that can be used in the arrays shown FIGS. 3 and 3A.
Figure 4A:
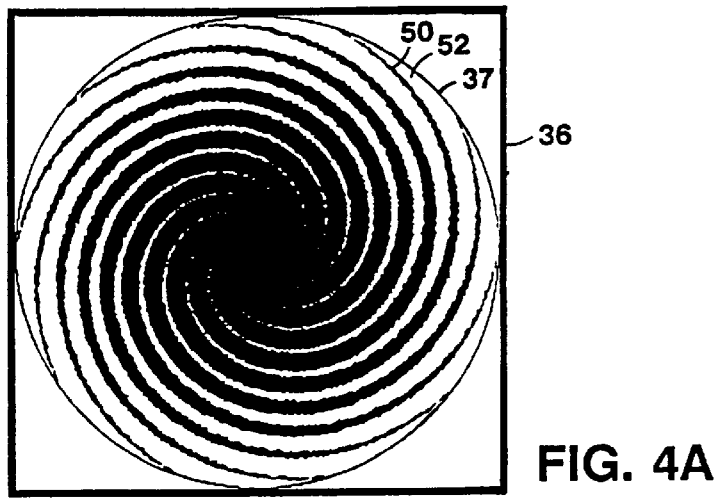
Figure 4B:
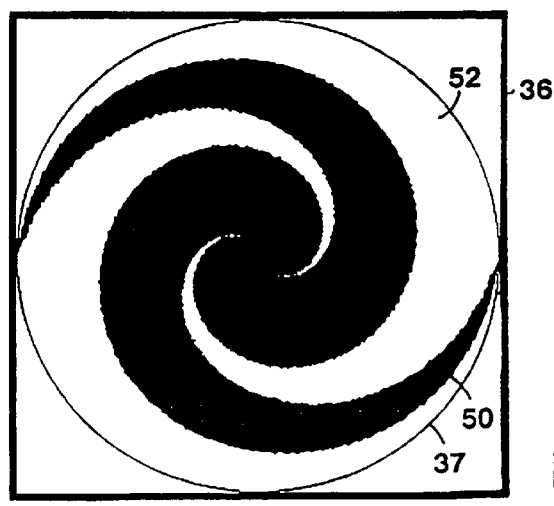

For example, in PRK procedures it is generally desirable to ablate corneal tissue in a circular ablation area. In such cases, a circular pattern is preferably selected for each optical profiling element, as shown in FIGS. 4–4B.

In another example, (e.g., in the fabrication of electronic circuits in the semiconductor industry) laser radiation is used to expose photosensitive resist layers in regions corresponding to portions of electronic circuits. In these applications, rectangular dimensions are generally preferred and thus rectangular patterns would be preferably chosen for each profiling element 36.

The array of profiling elements can be arranged as shown in FIG. 3, or alternatively as shown in FIG. 3A, for the circular profiling elements shown, every other row of the array of profiling elements can be shifted to achieve close-packing of the elements, and thus permit a greater amount of the initial laser beam to be employed in the corneal ablation process.

As shown in the embodiments of FIGS. 3 and 3A, each profiling element 36 includes a substantially identical filtering or intensity-modifying function of light-transmissive and non-transmissive regions.

This can be expressed mathematically as:

$$I = FI_0 \quad (1)$$

$$= F\Sigma e_i \quad (2)$$

$$= \Sigma F e_i \quad (3)$$

$$= \Sigma f_i e_i \quad (4)$$

wherein $I_0$ is the intensity profile of the overlap beams in the overlap plane 40 which have not been filtered (this beam tends to have a very flat beam profile), F is the filtering function provided by the beam profiler required to produce a resulting beam I having a desired intensity profile, $e_i$ represents the intensity profile of each of the constituent subbeams of the initial beam prior to interacting with the beam profiler (i.e., $I_0 = \Sigma e_i$), and $f_i$ represents the beam-modifying function provided by each of the profiling elements.

For an arbitrary initial beam that has an unknown beam profile, each of the $f_i$'s provides a very similar beam-modifying function as F. However, if the initial beam has a known intensity profile, this information can be used to optimize the beam-modifying functions of each of the profiling elements, so that each of the $f_i$'s need not necessarily be the same.

In certain preferred embodiments, the beam-modifying patterns are slightly rotated with respect to each other so that artifacts of the overlap of modified subbeams 38 achieves a smooth variation of light intensities in overlap plane 40 (i.e., so that the pattern of each profiling element are averaged out in the overlap plane).

The amount the beam-modifying pattern of each element is rotated relative to the patterns of the other elements is preferably determined by the number of profiling elements 36 employed in array 34 and the particular symmetry of the patterns. If N is the number of elements in the array of the type described, and B is e.g., the number of branches in each of the patterns, approximately 360°/(B·N) is the amount of relative rotation appropriate for each element to achieve optimal cancelling of the beam modification artifacts.

Embodiments have been designed that employ between about four and sixty-four profiling elements of the type described, each having about ten branches (e.g., see the patterns shown in FIG. 3), and in these designs the amount of relative rotation between the relative patterns preferably varies between about 9° and 0.55° respectively. A preferred embodiment has about sixteen profiling elements each having about ten branches, and a relative pattern rotation of about 2.25°.

It should be appreciated that rotation is not the only means of cancelling artifacts in the pattern of each profiling element in the overlap plane. Other schemes of overlapping subbeams with a desired intensity distribution in such a manner that the localized variations in the profile of each subbeam tend to cancel in the overlap plane, rather than reinforce each other, may be employed, depending upon e.g., the type and characteristics of the profiling elements employed.

Referring to FIGS. 4–4B, the patterns of the profiling elements are selected based upon the required intensity profile that achieves the desired refractive correction in the patient's cornea.

The variation in the light intensity of each subbeam depends upon the size of the smallest features of the selected profiling element pattern. For patterns which have relatively small features (e.g., as shown in FIG. 4), the intensity of each resulting subbeam 38 varies smoothly. Whereas for patterns with somewhat larger features (e.g., as shown in FIGS. 4A and 4B), the intensity variation of each resulting subbeam beam 38 is less smooth.

It is desirable that the coarseness (i.e., the feature size) of each profiling element pattern be selected to be small enough so that the respective intensity profile transferred to each subbeam 38 becomes averaged out by the intrinsic divergence of the beam by the time the subbeams reach the overlap plane 40.

For example, for an average feature size of about 2 mm, a beam divergence of 1 milli-radian, and assuming that at least eight of the profiling elements of profiler 34 are employed to achieve proper overlap cancellation of the subbeam artifacts, a distance of at least about 25 to 50 cm, between profiler 34 and overlap plane 40, is preferred.

It should be noted that the roughness of the patterns shown in FIGS. 4–4B are a result of the limits of the printing technology used to make the drawings, and is not desired. For example, computer-controlled mask fabrication techniques employed in the semiconductor industry, which can be used to fabricate the intensity-modifying patterns, are capable of much finer detail than the conventional printing techniques that were used to make the drawings shown herein.

The patterns of light-transmissive and non-transmissive regions are preferably fabricated by depositing a metal film upon a transparent substrate (e.g., glass or quartz) and defining the pattern of each element 36 by well-known semiconductor device processing techniques (e.g., chemical etching or metallization lift off).

In preferred embodiments, the transparent substrate is constructed out of material that is substantially transmissive to light in the operating wavelength range. For example, for UV laser radiation, the substrate is preferably fabricated from quartz, LiF, CaF, MgF or sapphire, while for visible or infra-red laser radiation, glass or low loss moldable plastic materials are preferably used.

Beam profiler 34 also includes a subbeam-directing optical system 54 for directing each subbeam 38 to overlap plane 40. Two preferred embodiments are shown in FIGS. 5–5B and 6–6A.

Figure 5:
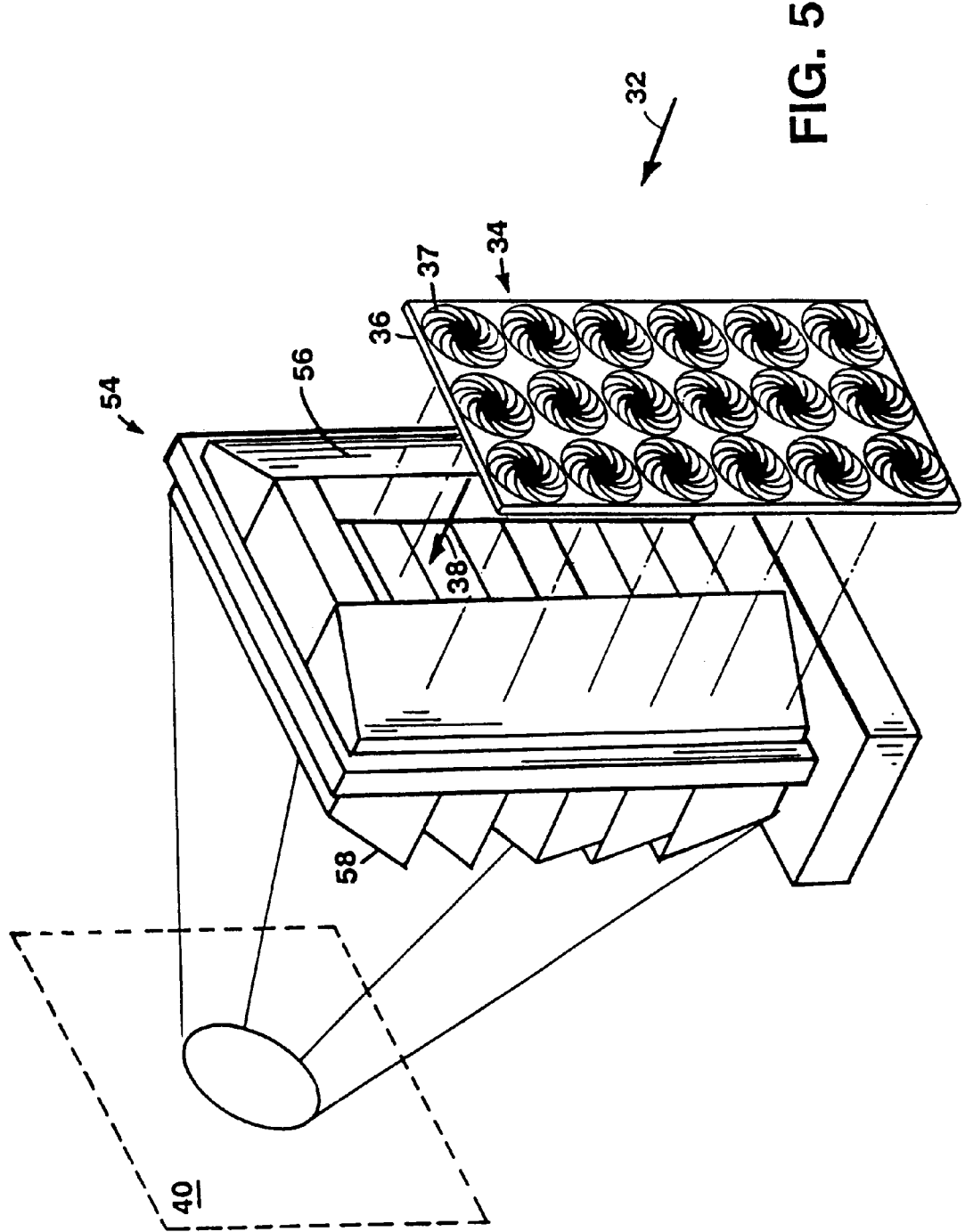
FIGS. 5 is a perspective view of a subbeam-directing optical system including overlapping prisms.
Figure 5B:
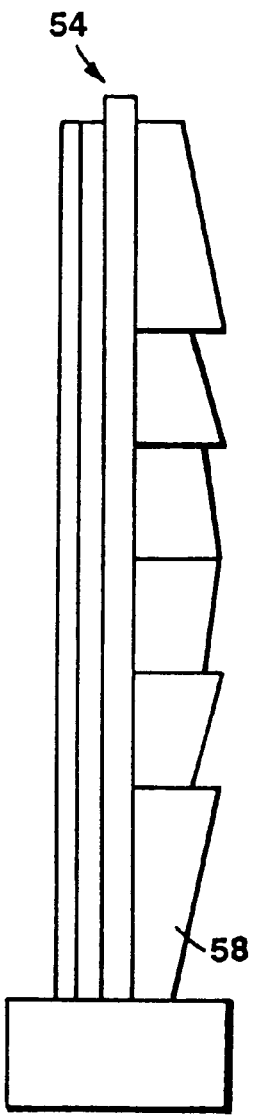
FIGS. 5A and 5B are elevational and side views, respectively, of a portion of the subbeam-directing optical system shown in FIG. 5.
Figure 5A:
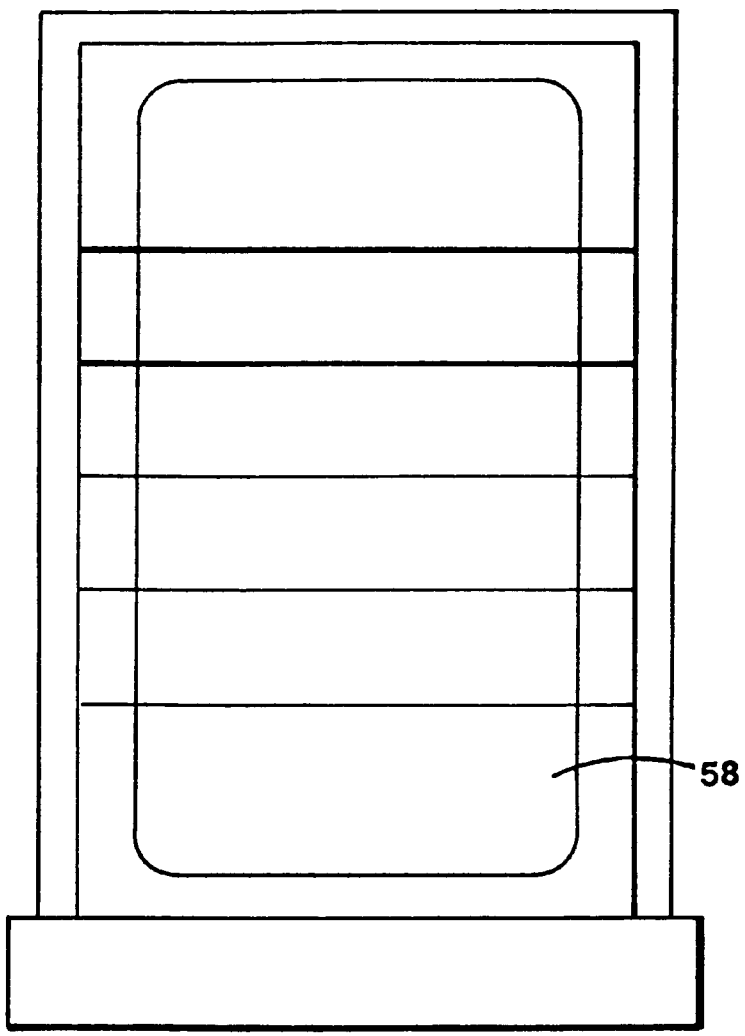

The subbeam-directing optical system shown in FIGS. 5–5B is implemented as two overlapped arrays of linear prisms 56, 58, which are rotated 90° with respect to each other, and which serve to direct each of the subbeams 38 to overlap plane 40.

Figure 6:
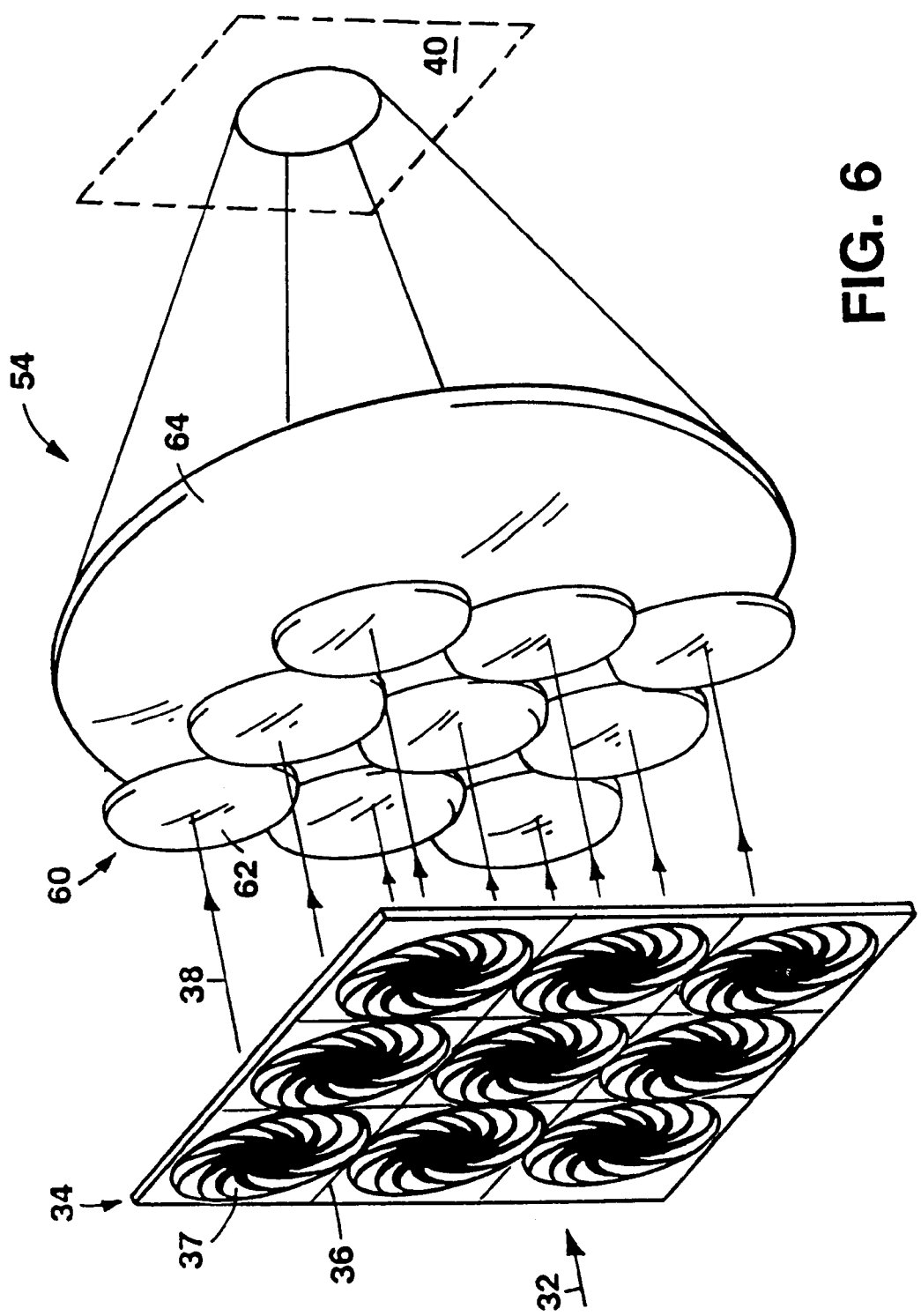
FIGS. 6 and 6A are perspective views of subbeam-directing optical systems including an array of lenses and a relatively large lens positioned adjacent the array and at a distance of about twice the focal distance of the array, respectively.
Figure 6A:
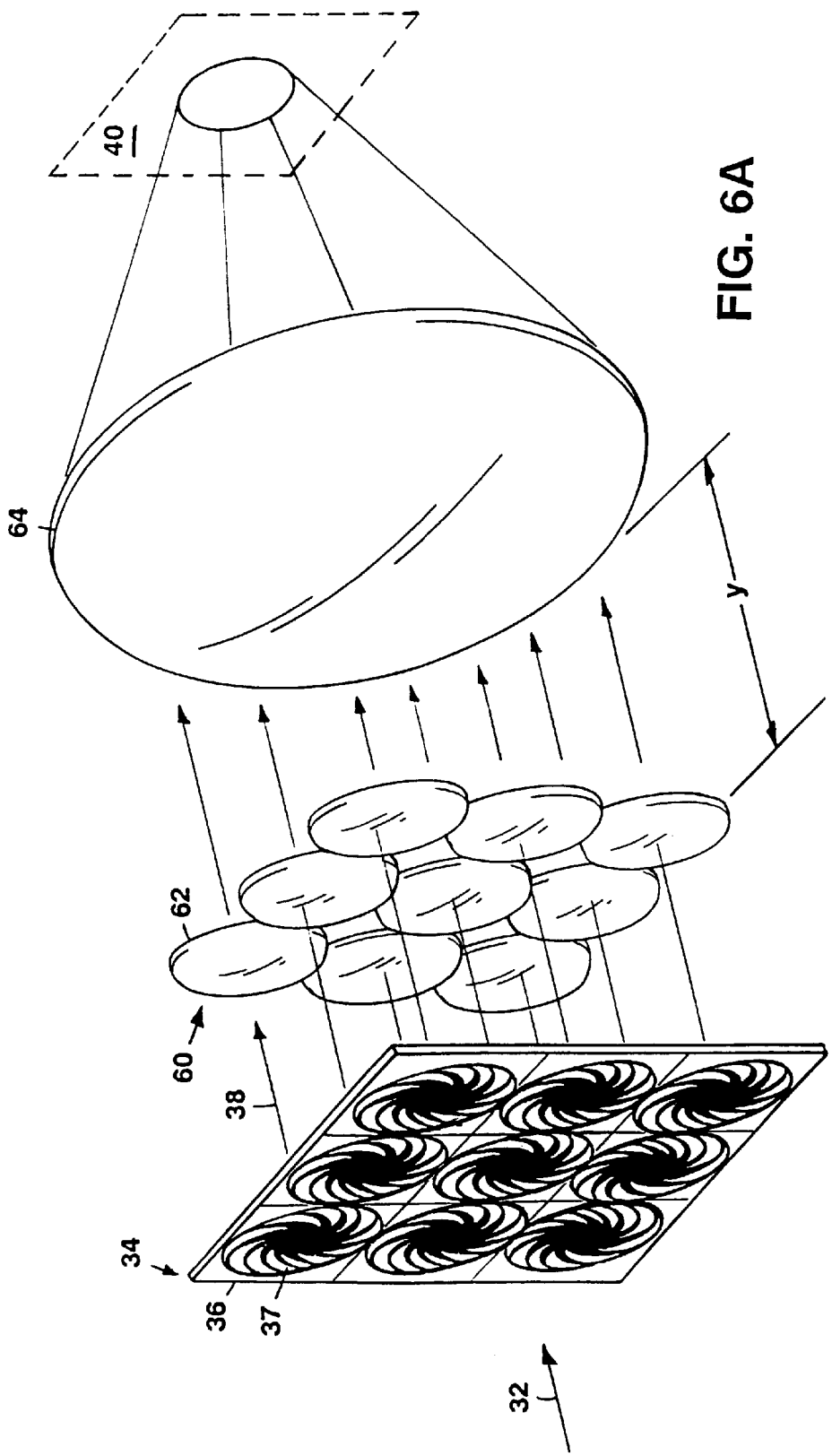

In alternative embodiments, shown in FIGS. 6 and 6A, subbeam-directing optical system 54 is implemented as an array 60 of relatively small lenses 62, each having an area about equal to the area of each profiling element 36 and each being located proximal to a respective profiling element 36, and a large focusing lens 64 that has an area large enough to receive each subbeam 38. Lens 64 can be located adjacent to array 60, as shown in FIG. 6, or alternatively, lens 60 can be located at a distance Y from array 60 that is about twice the focal distance of each lens 62, as shown in FIG. 6A.

The inventor notes that for the embodiment shown in FIG. 6A, in which lens 64 is adjacent array 60, focusing lens 64 can be located on either side of array 60.

FIGS. 7 and 7A show two selected light intensity profiles of photoablation beam 10, as a function of cross-sectional coordinates (u,v), for photorefractive corrective treatment of myopia and hyperopia, respectively, according to the invention. In these embodiments, photoablation beam 10 typically has, e.g., a circular cross-section and a smoothly varying intensity profile with a selected threshold value 66.

For the myopic correction (FIG. 7), the highest light intensity is delivered in the central region 68 of the cornea to cause relative flattening of the corneal surface.

For the hyperopic correction (FIG. 7A), increased ablation is needed in the annular perifocal region to cause an increase in the corneal curvature. Thus, the light intensity distribution has a maximum in an annular region 70 and a local minimum in the central region 72.

FIGS. 7B and 7C show two selected light intensity profiles of photoablation beam 10, as a function of cross-sectional coordinates (u,v), for photorefractive corrective treatment of two different astigmatic conditions. The profile shown in FIG. 7B has mostly astigmatic axial components, while the profile shown in FIG. 7C has both hyperopic and myopic astigmatic axial components.

In addition, other intensity profiles can be selected for specific procedures, such as removing corneal ulcers.

For example, an arbitrary intensity profile 74 is shown in FIG. 7D. Intensity profile 74 has a maximum in a region 76 to create preferential ablation and a decreasing intensity profile along a corresponding axis 77. It should be noted that this profile is not intended to be used for corneal ablation. Rather, profile 74 is merely presented to illustrate an example of an intensity profile that can be generated by a beam profiler designed according to the invention.

The beam intensity profiles shown in FIGS. 7–7D are merely intended to be illustrative of the general features of the intensity distributions that can be used to treat the above-mentioned refractive problems. Proper beam profiles, e.g., at the periphery blend zones, would be selected by surgeons performing PRK procedures based upon patient needs.

Suitable irradiation intensities vary depending on the wavelength of the laser radiation and the nature of the irradiated surface. For any given wavelength of laser radiation applied to the corneal layers, there is typically a threshold value of energy density below which significant ablation does not occur. Above this threshold density, there will be a range of energy density over which increasing energy densities provide increasing depths of ablation, until a saturation point is reached, above which no significant increase in ablation rate occurs.

Most preferably, the laser system is used to provide an initial beam that has an energy density at the corneal surface of slightly less than the saturation value. Thus, when ablating the cornea with a wavelength of 193 nm, it is preferable to provide pulses of radiation that have an energy density of about 100–150 mJ cm$^{-2}$ per pulse. Typically, a single pulse of this energy distribution will ablate a depth in the range of about 0.1–3 $\mu$m.

Wavelengths in the range of about 300 nm to about 1400 nm should not be used, as this radiation tends to penetrate the eye and damage the cells lying below the stromal layer of the cornea.

It is preferable to determine the ablation rate of stromal tissue in order to properly shape the stroma, so that optimal ablation can be achieved, while minimizing damage caused by thermal heating of the corneal tissue.

The laser pulse rate is preferably selected to be low enough to allow the ophthalmologist to perform accurate ablation of the corneal tissue, while at the same time the rate is preferably chosen to be high enough so that the procedure may be performed in a reasonable amount of time. The pulse repetition rate is normally less than about 100 Hz, and preferably the rate is selected to be between about 10 and 40 Hz.

Referring to FIG. 8, the treatment according to the present invention first requires the precise determination of a desired post treatment shape that provides proper correction of the patient's vision (78).

Once the patient's eyesight is evaluated and the desired change of the corneal surface is determined, controller 24 receives topographic data of a starting profile and a desired final profile (80). Based on the topographic data, the controller determines the spatial dependence of a tissue depth needed to be achieved by the ablation process (82). The system recalls a value of the ablation depth of a single pulse (84) and determines the number of pulses needed to achieve the final profile (86).

The final profile also depends upon the intensity profile of the ablation beam (88). The intensity profile is selected by selecting the transmission pattern, i.e., the pattern of light-transmissive and non-transmissive regions, as determined by appropriate mathematical formulae. The pattern for each profiling element 36 is selected from a set of prefabricated optical arrays each having a different pattern of intensity-defining elements (90). A computer-aided photolithographic process is used to fabricate the array of patterns of intensity-defining elements 36 that produce the selected intensity profile.

The selected intensity-defining array of patterns is then used to create the ablation beam used in the PRK procedure (92).

Before the PRK photoablation is initiated, the patient's eye is anesthetized using a topical anesthetic and an eyelid speculum is used to retract the eyelid. An eyepiece with an engagement structure is placed onto the eye ball and the eye is fixated and aligned with respect to subbeam delivery system 18.

After laser 22 reaches desired operation parameters (i.e., the light intensity per pulse, repetition rate, etc.), the epithelium is generally removed (e.g., either surgically or using a preselected dose of photoablative radiation). A predetermined number of the pulses, as determined in step 86, above, are delivered to the corneal surface 12 to ablate and thus shape the stroma.

In certain preferred embodiments, the system include a gas flushing attachment for removing the ablated debris. After the ablation procedure is performed, the corneal surface is rinsed with BSS solution and steroids including pain-reducing compounds. Antibiotics may be also applied topically and an eye patch is worn for several days.

In preferred embodiments, the laser ablation system is fully automated and includes a corneal topographer and a vision evaluation system, both adapted to determine the desired changes in the corneal shape. Controller 24 receives the measured data and compares the measured and desired corneal shapes and determines a dose of photoablation radiation required across the corneal surface, as well as the number of pulses required of the laser source.

The controller also selects the required array of patterns of profiling elements 36, to create the ablation beam with the desired intensity profile.

The corneal topographer may also be used after partial corneal reformation to determine the current corneal curvature. The updated information is then used to control further ablation of the corneal surface.

The measured data and the beam parameters may also be displayed on a monitor or a printer during or after the laser ablation.

The patterns of intensity-defining elements 36 can be created dynamically, e.g., by applying the technology used in the flat panel displays, in which individual light absorbing domains are oriented using an electric field.

Alternatively, subbeams 38 with desired intensity distributions may also be created using binary optic or holographic techniques.

Referring to FIG. 9, the corneal ablation system may utilize a light reflecting array 100, instead of a light transmitting array to create ablation beam 10. The profiling elements 102 of array 100 modify and reflect the individual subbeams of photoablation beam 10.

Light-directing elements 106 reflect corresponding subbeams 38 and direct them along a proper beam path toward overlap plane 40. The intensity-defining pattern of each profiling element 102 modifies the light intensity of subbeams 38 using a plurality of light reflecting domains and a plurality of complementary absorbing (or transmitting) domains. As described above, the reflecting and absorbing beam elements are again constructed and arranged to provide a selected filtering function.

Other embodiments are within the scope of the claims.

What is claimed is:

1. An optical beam profiler for creating, from an initial beam of radiation, a resulting beam of radiation having a desired intensity profile, said profiler comprising;

an intensity modifier including an array of intensity-modifying profiling elements each comprising a predetermined pattern of radiation transmissive and non-transmissive regions, said patterns determined in accordance with selected intensity-modifying functions, each intensity-modifying profiling element being disposed to independently modify and filter a different subbeam portion of the initial beam to thereby create respective intensity-modified subbeams each having a respective predetermined intensity profile so that overlapping of said respective intensity-modified subbeams in an overlap plane produces said desired intensity profile; and A subbeam-directing optical system constructed and arranged to direct said subbeams along respective subbeam paths that overlap in said overlap plane, said resulting beam of radiation being created at the overlap plane, its said desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of said overlapping subbeams, the intensity profile of said resulting beam being determined by the intensity modifying functions of said selected intensity-modifying profiling elements.

2. The optical beam profiler of claim 1 further comprising a subbeam delivery system for re-imaging said overlap plane onto an image plane at a target surface.

3. The optical beam profiler of claim 2 wherein said subbeam-directing optical system comprises first and second rectangular prisms oriented at ninety degrees relative to each other.

4. The optical beam profiler of claim 2 wherein said subbeam-directing optical system comprises an array of lenses each constructed and arranged to receive one of said subbeams, and a second lens constructed and arranged to receive each of said subbeams, said array of lenses and said second lens being configured to substantially direct each of said subbeams to overlap in said overlap plane.

5. The optical beam profiler of claim 4 wherein said second lens is located either adjacent said array or at a distance from said array equal to about twice the focal distance of the lenses of said array.

6. The optical beam profiler of claim 1 wherein said array of intensity-modifying profiling elements are disposed at selected spatial locations relative to the initial beam.

7. The optical beam profiler of claim 6 wherein said subbeam-directing optical system is constructed and arranged to overlap said subbeams at the overlap plane a sufficient distance from said array of profiling elements for localized intensity profile variations in each of said subbeams, introduced by said profiling elements, to become substantially averaged-out at the overlap plane as a result of intrinsic divergence in the initial beam of radiation.

8. The optical beam profiler of claim 6 wherein said patterns are constructed and arranged to produce corresponding subbeams modified according to substantially identical intensity-modifying functions.

9. The optical beam profiler of claim 8 wherein said patterns are configured to produce corresponding subbeams that are oriented with respect to each other in a manner characterized in that the local intensity profile variations of each of said subbeams substantially cancel in the optical incoherent summation that results at the overlap plane.

10. The optical beam profiler of claim 6 wherein said array of profiling elements is close-packed.

11. The optical beam profiler of claim 10 wherein said profiling elements in said array are substantially identical in size and shape.

12. The optical beam profiler of claim 6 wherein said patterns are configured to produce subbeams having cross-sectional shapes substantially corresponding to a desired cross-sectional shape of said resulting beam.

13. The optical beam profiler of claim 12 wherein said patterns are configured to produce subbeams having circular cross-sectional shapes.

14. A PRK laser ablation system for selectively ablating corneal tissue of a patient's eye in an ablation area to produce a desired corneal shape, said ablation system comprising:

a source of an initial beam of radiation; and a beam profiler, interposed between said source and the patient's eye, comprising an array of intensity-modifying profiling elements, each of said profiling elements comprising a predetermined pattern of radiation reflecting and non-reflecting regions, each of said profiling elements disposed to modify and filter a different respective subbeam portion of the initial beam to thereby create respective intensity-modified subbeams each having a respective predetermined modified intensity profile so that overlapping of said respective intensity-modified subbeams in an overlap plane produces said desired intensity profile, said beam profiler being constructed and arranged to direct said subbeams along respective subbeam paths that overlap in an overlap plane, a resulting beam of radiation being created at the overlap plane that has a desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of said overlapping subbeams, the intensity profile of said resulting beam selected to produce the desired corneal shape in the patient's eye.

15. A PRK laser ablation system for selectively ablating corneal tissue of a patient's eye in an ablation area to produce a desired corneal shape, said ablation system comprising:
   a source of an initial beam of radiation; and
   a beam profiler, interposed between said source and the patient's eye, comprising an array of intensity-modifying profiling elements, each element including a predetermined pattern of radiation transmissive and radiation non-transmissive regions, each element disposed to modify and filter a different respective subbeam portion of the initial beam to thereby create respective intensity-modified subbeams each having a respective predetermined modified intensity profile so that overlapping of said respective intensity-modified subbeams in an overlap plane produces said desired intensity profile, said beam profiler being constructed and arranged to direct said subbeams along respective subbeam paths that overlap in an overlap plane, a resulting beam of radiation being created at the overlap plane that has a desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of said overlapping subbeams, the intensity profile of said resulting beam selected to produce the desired corneal shape in the patient's eye.

16. The PRK ablation system of claim 15 further comprising a subbeam delivery system for re-imaging said overlap plane onto an image plane at the ablation area.

17. The PRK ablation system of claim 15 wherein said beam profiler is constructed and arranged to produce said resulting beam having an intensity profile to ablate a shape in the corneal surface of the patient's eye suitable to treat myopia, hyperopia, or astigmatism.

18. The PRK ablation system of claim 15 wherein said beam profiler is constructed and arranged to produce said resulting beam having an intensity profile suitable to remove irregular growth on the corneal surface.

19. A method for creating, from an initial beam of radiation, a resultant beam of radiation having a desired intensity profile, comprising the steps of:
   generating said initial beam of radiation along a beam path;
   receiving said initial beam with an intensity modifier in the beam path, said intensity modifier including an array of intensity-modifying profiling elements, each of the profiling elements comprising a predetermined pattern of radiation transmissive and non-transmissive regions, said patterns determined in accordance with selected intensity-modifying functions;
   independently modifying and filtering the intensity profile of a different respective portion of the initial beam with the respective profiling elements to create respective intensity-modified subbeams each having a respective predetermined intensity profile so that overlapping of said respective intensity-modified subbeams in an overlap plane produces said desired intensity profile;
   directing the subbeams along respective subbeam paths that overlap in an overlap plane; and
   creating the resulting beam of radiation at the overlap plane that has said desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of said overlapping subbeams, the intensity profile of said resulting beam being determined by the selected intensity-modifying functions of the intensity-modifying profiling elements.

20. A method for creating, from an initial beam of radiation, a resultant beam of radiation having a desired intensity profile, comprising the steps of:
   generating said initial beam of radiation along a beam path;
   receiving said initial beam with an intensity modifier in the beam path, said intensity modifier including an array of intensity-modifying profiling elements; each of the profiling elements comprising a predetermined pattern of radiation reflecting and non-reflecting regions, said patterns determined in accordance with selected intensity-modifying functions;
   independently modifying and filtering intensity profiles of different portions of the initial beam with the respective profiling elements to create respective intensity-modified subbeams each having a respective predetermined intensity profile so that overlapping of said respective intensity-modified subbeams in an overlap plane produces said desired intensity profile;
   directing the subbeams along respective subbeam paths that overlap in an overlap plane; and
   creating the resulting beam of radiation at the overlap plane that has said desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of said overlapping subbeams, the intensity profile of said resulting beam being determined by the selected intensity-modifying functions of the intensity-modifying profiling elements.

21. An optical beam profiler for creating from an initial beam of radiation a resulting beam of radiation having a desired intensity profile, said profiler comprising:

an intensity modifier including an array of intensity-modifying profiling elements each comprising a predetermined pattern of radiation reflecting and non-reflecting regions, said patterns determined in accordance with selected intensity-modifying functions, said elements of said array disposed to independently modify and filter different subbeam portions of the initial beam to thereby create respective intensity-modified subbeams each having a respective predetermined intensity profile so that overlapping of said respective intensity-modified subbeams in an overlap plane produces said desired intensity profile; and a subbeam-directing optical system constructed and arranged to direct said respective subbeams along respective subbeam paths that overlap in an overlap plane, said resulting beam of radiation being created at the overlap plane, its said desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of said overlapping subbeams, the intensity profile of said resulting beam being determined by the intensity-modifying functions of the selected intensity modifying profiling elements.

22. A method of selectively ablating corneal tissue of a patient's eye in an ablation area to produce a desired corneal shape, said method comprising the steps of:

(a) providing an initial beam of radiation;

(b) independently modifying and filtering intensity profiles of different subbeam portions of the initial beam with an array of intensity-modifying profiling elements, each profiling element comprising a predetermined pattern of radiation transmissive and non-transmissive regions, to thereby create respective intensity-modified subbeams each having a respective predetermined modified intensity profile so that overlapping of said respective intensity-modified subbeams in an overlap plane produces said desired intensity profile;

(c) directing said subbeams along respective subbeam paths that substantially overlap in an overlap plane;

(d) creating a resulting beam of radiation with said overlapping subbeams at the overlap plane, the resulting beam having a desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of the overlapping subbeams, said intensity profile being selected to produce the desired corneal shape in the patient's eye; and (e) ablating the corneal tissue of the patient's eye with the resulting beam.

23. A method of selectively ablating corneal tissue of a patient's eye in an ablation area to produce a desired corneal shape, said method comprising the steps of:

(a) measuring optical parameters of the patient's eye;

(b) selecting a desired intensity profile of an ablation beam for shaping the patient's cornea based upon the measured optical parameters and the desired corneal shape;

(c) selecting an intensity modifier based upon the desired intensity profile, said intensity modifier comprising an array of intensity-modifying profiling elements, each profiling element comprising a selected pattern of radiation transmissive and non-transmissive regions;

(d) providing an initial beam of radiation;

(e) independently modifying and filtering the intensity profile of different subbeam portions of the initial beam with respective ones of said profiling elements to thereby create respective intensity-modified subbeams each having a respective predetermined modified intensity profile so that overlapping of said respective intensity-modified subbeams in an overlap plane produces said desired intensity profile;

(f) directing said subbeams along respective subbeam paths to overlap in an overlap plane;

(g) forming a resulting beam of radiation with said overlapping subbeams at the overlap plane, the resulting beam having a desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of the overlapping subbeams;

(h) guiding said resulting beam of radiation to the ablation area; and (i) ablating the corneal tissue in a manner to produce the desired corneal shape.

24. The method of claim 23 further comprising the step of examining the shaped corneal surface.

25. The method of claim 23, further comprising the steps of repeating steps (a)–(j) to further shape the corneal surface.

26. A method of selectively ablating corneal tissue of a patient's eye in an ablation area to produce a desired corneal shape, said method comprising the steps of:

(a) providing an initial beam of radiation;

(b) independently modifying intensity profiles of different subbeam portions of the initial beam with an array of intensity-modifying profiling elements, each profiling element comprising a predetermined pattern of radiation reflecting and non-reflecting regions, to thereby create respective intensity-modified and filtered subbeams each having a respective predetermined modified intensity profile so that overlapping of said respective intensity-modified subbeams in an overlap plane produces said desired intensity profile;

(c) directing said subbeams along respective subbeam paths that substantially overlap in an overlap plane;

(d) creating a resulting beam of radiation with said overlapping subbeams at the overlap plane, the resulting beam having a desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity profiles of the overlapping subbeams, said intensity profile being selected to produce the desired corneal shape in the patient's eye; and (e) ablating the corneal tissue of the patient's eye with the resulting beam.

27. A method of selectively ablating corneal tissue of a patient's eye in an ablation area to produce a desired corneal shape, said method comprising the steps of:

(a) measuring optical parameters of the patient's eye;
(b) selecting a desired intensity profile of an ablation beam for shaping the patient's cornea based upon the measured optical parameters and the desired corneal shape;
(c) selecting an intensity modifier based upon the desired intensity profile, said intensity modifier comprising an array of intensity-modifying profiling elements, each profiling element comprising a selected pattern of radiation reflecting and non-reflecting regions;
(d) providing an initial beam of radiation;
(e) independently modifying and filtering the intensity profile at different subbeam portions of the initial beam with respective ones of said profiling elements to thereby create respective intensity-modified subbeams each having a respective predetermined modified intensity profile so that overlapping of said respective intensity-modified subbeams in an overlap plane produces said desired intensity profile;
(f) directing said subbeams along respective subbeam paths to overlap in an overlap plane;
(g) forming a resulting beam of radiation with said overlapping subbeams at the overlap plane, the resulting beam having a desired intensity profile produced by overlapping said respective intensity-modified subbeams in an overlap plane, said overlapping of said respective intensity-modified subbeams resulting from superimposing said subbeams in said overlap plane, said desired intensity profile being equal to an optical incoherent summation of the modified intensity of profiles of the overlapping subbeams;
(h) guiding said resulting beam of radiation to the ablation area; and
(i) ablating the corneal tissue in a manner to produce the desired corneal shape.

\* \* \* \* \*